United States Patent [19]

Kenyon et al.

[11] Patent Number: 4,680,417
[45] Date of Patent: Jul. 14, 1987

[54] 2.6-DIOXO-2.6-DEHYDROBENZO[1:2-B,4:5-B]DIFURANS

[75] Inventors: Ronald W. Kenyon, Manchester; Derek Thorp, Heywood, both of England

[73] Assignee: Imperial Chemical Industries Plc, London, England

[21] Appl. No.: 792,645

[22] Filed: Oct. 29, 1985

[30] Foreign Application Priority Data

Nov. 19, 1984 [GB] United Kingdom ................ 8429170

[51] Int. Cl.$^4$ ........................................... C07D 493/14
[52] U.S. Cl. ..................................... 549/299; 549/47; 549/45; 548/431; 548/433
[58] Field of Search ........................................ 549/299

[56] References Cited

U.S. PATENT DOCUMENTS 4,115,404  9/1978  Greenhalgh ........................ 549/299
4,122,087  10/1978 Greenhalgh ........................ 549/299

FOREIGN PATENT DOCUMENTS 0033583  1/1981  European Pat. Off. .
0146269  6/1985  European Pat. Off. .
2103213  2/1983  United Kingdom .
2151611  11/1984 United Kingdom .

Primary Examiner—Jane T. Fan
Attorney, Agent, or Firm—Cushman, Darby & Cushman

[57] ABSTRACT

A compound of the formula:

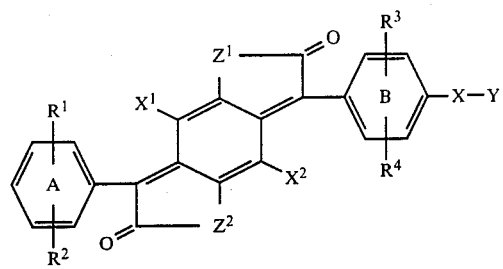

wherein, $Z^1$ and $Z^2$ are each independently $-O-$, $-S-$ or $-NR^5-$ in which $R^5$ is H or an optionally-substituted hydrocarbon group or an acyl group;

$X^1$ and $X^2$ are selected from H, halogen, cyano, $C_{1-4}$-alkyl, $C_{1-4}$-alkoxy, aryl, carbamoyl, sulphamoyl, carboxylic acid or carboxylic acid ester;

$R^1$ to $R^4$ are each independently selected from H, $C_{1-4}$-alkyl, $C_{1-4}$-alkoxy, $C_{1-4}$-alkenyl, halogen and the group $-X-Y$;

X is $-O-$ or $-S-$; and

Y is $C_{2-10}$-alkenyl provided that, the substituents on rings A and B are different when $Z^1$ and $Z^2$ are the same or that $Z^1$ and $Z^2$ are different when the substituents on rings A and B are the same, which is suitable for the coloration of synthetic textile materials and processes for its preparation.

7 Claims, No Drawings

2,6-DIOXO-2,6-DEHYDROBENZO[1:2-B,4:5-B]DIFURANS

This specification describes an invention relating to a novel hetero-polycyclic compound, a method for its preparation and its use in the colouration of textile materials.

According to the present invention there is provided a compound of the formula:

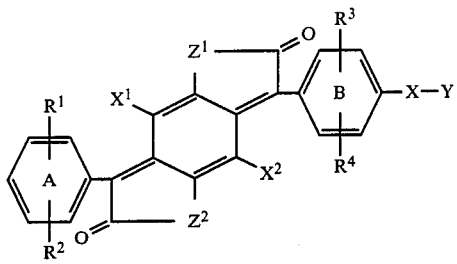

wherein, $Z^1$ and $Z^2$ are each independently —O—, —S— or —NR$^5$— in which R$^5$ is H or an optionally-substituted hydrocarbon group or an acyl group;

$X^1$ and $X^2$ are selected from H, halogen, cyano, $C_{1-4}$-alkyl, $C_{1-4}$-alkoxy, aryl, carbamoyl, sulphamoyl, carboxylic acid or carboxylic acid ester;

$R^1$ to $R^4$ are each independently selected from H, $C_{1-4}$-alkyl, $C_{1-4}$-alkoxy, $C_{1-4}$-alkenyl, halogen and the group —X—Y;

X is —O— or —S—; and

Y is $C_{2-10}$-alkenyl provided that, the substituents on rings A and B are different when $Z^1$ and $Z^2$ are the same or that $Z^1$ and $Z^2$ are different when the substituents on rings A and B are the same.

The optionally substituted hydrocarbon group represented by R$^5$ is preferably, $C_{1-8}$-alkyl, and more preferably $C_{1-4}$-alkyl, or monocyclic aryl, more preferably phenyl which may be substituted by groups selected from hydroxy, halogen, nitro and alkoxy. Where R$^5$ is monocyclic aryl it may also be substituted by alkyl and where R$^5$ is alkyl it may also be substituted. The acyl group represented by R$^5$ is preferably $C_{1-4}$-alkyl- or monocyclic aryl-carbonyl or sulphonyl which may be substituted by one or more groups selected from hydroxy, halogen, nitro, $C_{1-4}$-alkyl and $C_{1-4}$-alkoxy. Examples of the optionally substituted hydrocarbon groups represented by R$^5$ are alkyl and preferably $C_{1-4}$-alkyl, such as methyl, ethyl, n-propyl and iso-propyl; substituted alkyl, preferably substituted $C_{1-4}$-alkyl, such as beta-hydroxyethyl, beta-methoxyethyl and beta-ethoxyethyl; phenyl and substituted phenyl such as tolyl, chlorophenyl, nitrophenyl and $C_{1-4}$-alkoxyphenyl. Examples of the acyl groups represented by R$^5$ are acetyl, propionyl, n-butyryl, iso-butyryl, benzoyl and m-nitrobenzoyl, p-chlorobenzoyl, p-methylbenzoyl, p-methoxybenzoyl and p-hydroxybenzoyl.

The aryl groups represented by $X^1$ and $X^2$ are preferably mono-homocyclic aryl, that is phenyl and substituted phenyl. The $C_{1-4}$-alkyl and alkoxy groups represented by $X^1$ and $X^2$ may also be substituted and examples of suitable substituents for these and the aryl groups are hydroxy, halogen, nitro, $C_{1-4}$-alkyl and $C_{1-4}$-alkoxy. The carbamoyl and sulphamoyl groups represented by $X^1$ and $X^2$ are preferably of the formula —CONL$^1$L$^2$ or —SO$_2$NL$^1$L$^2$ wherein L$^1$ and L$^2$ are each independently hydrogen, $C_{1-4}$-alkyl or monocyclic aryl, preferably phenyl. The carboxylic acid ester groups represented by $X^1$ and $X^2$ are preferably of the formula —COOL$^3$ wherein L$^3$ is optionally substituted alkyl, especially $C_{1-4}$-alkyl, or monocyclic aryl, especially phenyl.

Benzene rings A and B are preferably different, the difference lying in the nature and/or the number of substituents carried by each ring. The difference lies preferably in the identity of the groups R$^1$ to R$^4$ and —X—Y carried by these rings. It is preferred that R$^1$ and R$^2$ are both H or both $C_{1-4}$-alkyl or that one is $C_{1-4}$-alkyl or alkoxy and the other is H and that the substituent is present in a para position. It is preferred that R$^3$ and R$^4$ are both H or both $C_{1-4}$-alkyl or that one is $C_{1-4}$-alkyl or $C_{1-4}$-alkoxy and the other is H and that the substituent is present in an ortho position with respect to the group —X—Y.

It is preferred that $X^1$ and $X^2$ are both hydrogen and it is also preferred that $Z^1$ and $Z^2$ are both oxygen. Under these preferred circumstances the asymmetry in the compound of Formula I is provided by a difference in substitution on benzene rings A and B. It is preferred that ring A is unsubstituted, or carries a single alkyl or alkoxy group in the para position, and that ring B carries a single substituent represented by —X—Y.

It is preferred that X is oxygen and it is further preferred that Y is $C_3$- or $C_4$-alkenyl. Examples of suitable groups represented by Y are allyl, beta-methylallyl and n-but-2-enyl.

The compound of Formula I, wherein $Z^1$ and $Z^2$ are both oxygen, may be prepared by reaction of a 5-hydroxy-2-oxo-3-phenyl-2,3-dihydrobenzofuran of the formula:

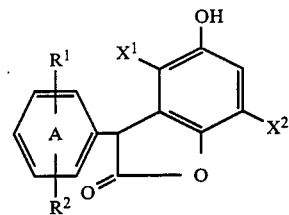

in which $X^1$, $X^2$, $R^1$, $R^2$ and A have the same meaning as in Formula I, with a mandelic acid or derivative thereof, in which the 3-phenyl substituent of the dihydrobenzofuran and/or the phenyl ring of the mandelic acid carry appropriate substituents, at least one of which is a group —X—Y in the 4-position, in an organic solvent at a temperature not exceeding 120° C. in the presence of an acid catalyst and oxidising the product with a mild oxidising agent.

A preferred process for the preparation of a compound of Formula I comprises the reaction of a compound of Formula IV with a mandelic acid or derivative thereof of the formula:

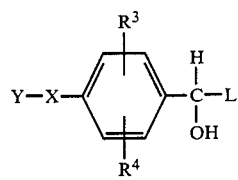

wherein X and Y have the same meanings as in Formula I and L is COOR[6], CONR[7]R[8] or CN, in which R[6], R[7] and R[8] are each independently H or $C_{1-4}$-alkyl under the aforementioned conditions and oxidising the intermediate product to form a compound of Formula I.

Another preferred process comprises the reaction of a 3,7-diphenyl-2,6-dioxo-2,6-dihydro-benzodifuran in which one of the phenyl substituents carries a group —XH in the 4-position, i.e. a compound as defined in Formula I except that Y is H, with (i) a compound, U—Y wherein Y is as defined in Formula I above and U is a halogen atom, preferably chlorine or bromine, in an organic solvent containing an acid binding agent or (ii) an ester of an alcohol Y—OH and an acid, preferably an acid which is easily displaced, such as 4-methylbenzenesulphonic acid.

The reaction in an organic solvent is preferably performed at a temperature from 60°–100° C. Suitable organic solvents are alkane carboxylic acids and their anhydrides such as acetic acid, formic acid, propionic acid and acetic anhydride; hydrocarbons and halogenated hydrocarbons such as, toluene, xylene, mesitylene, benzene, low boiling petroleum fractions, chlorobenzene, dichlorobenzene, trichlorobenzene, bromotoluene, chloronaphthalenes, dichloroethane and tetrachloroethane; nitrated hydrocarbons such as nitromethane, nitrotoluene and nitrobenzene; sulpholane; ketones such as methyl-isobutyl ketone; ethers such anisole and diphenyl ether; and esters such as methyl benzoate. Suitable acid catalysts are organic sulphonic acids such as p-toluenesulphonic acid, benzenedisulphonic acid and methanesulphonic acid; mineral acids such as hydrochloric acid; and Lewis acids such as ferric chloride and stannic chloride. A preferred reaction system comprises an organic solvent such as tetrachloroethane, acetic acid, chlorobenzene or toluene as solvent and p-toluenesulphonic acid as catalyst. Any convenient oxidising agent for dehydrogenating a carbon-carbon single bond may be employed for the oxidation step. Examples of suitable oxidising agents are chloranil, bromanil, benzoquinone, naphthoquinone, anthraquinone, metavanadates, persulphates, dichromates, chlorates perborates and periodates, hydrogen peroxide, vanadium pentoxide, lead and manganese dioxides and atmospheric oxygen.

The compounds of Formula IV may be prepared by the reaction of mandelic acid, or a derivative thereof, with hydroquinone, using a method described in EP 33583A. The compound of Formula I in which —X—Y is OH may be prepared by reaction of 4-hydroxymandelic acid with a compound of Formula IV using a method giving in EP 33583A.

Although saturated analogues of the present compound, i.e. compounds of Formula I except that —X—Y is alkoxy, are known from UK 1,568,231 and EP 33583A, it is not possible to prepare a dye of Formula I by the processes disclosed in these patents.

A compound of Formula I is suitable for the coloration of synthetic textile materials, especially polyesters, giving bright orange to bluish red shade. It has a high extinction coefficient in the region of 450 to 550 nm and generally builds up well on the textile material to give a strong shade. It has good light fastness and very good wet and heat fastness properties. It is generally suitable for application by recognised dyeing and printing techniques for polyester textile materials.

According to another feature of the present invention there is provided a process for the colouration of a synthetic textile material which comprises dyeing or printing the synthetic textile material with a dyebath liquor or a print paste containing an aqueous dispersion of a compound according to Formula I. Such processes for applying the compound of Formula I to synthetic textile material are more specifically described in EP 33583A.

The invention is further illustrated by the following examples in which all parts and percentages are by weight unless otherwise indicated.

EXAMPLE 1

A mixture of 1.13 g of 5-hydroxy-2-oxo-3-phenyl-2,3-dihydrobenzofuran, 1.04 g of 4-allyloxymandelic acid, 0.95 g of p-toluenesulphonic acid and 15 ml of 1,1,2,2-tetrachloroethane was stirred at 70°–80° C. for 6 hours. 1.23 g of chloranil was then added and the mixture heated at 70°–80° C. for 1 hour. After cooling to 25° C., 50 ml of methanol was added and the precipitated product 3-phenyl-7-(4-allyloxyphenyl)-2,6-dioxo-2,6-dihydrobenzo[1:2-b, 4:5-b']difuran filtered off, washed successively with methanol, water, methanol and dried. The product (yield 1.0 g) dissolved in chloroform to give a red solution having an absorption maximum at 501 nm.

When applied to aromatic polyester textile materials from an aqueous dispersion the product gives very bright strong red shades with good light fastness and excellent fastness to heat and wet treatments.

When applied to polyester and polyester-cotton blends from print pastes by recognised printing techniques red shades are produced with good all round fastness properties.

The 4-allyloxymandelic acid was prepared by heating a mixture of 33.6 g of 4-hydroxymandelic acid, 26.6 g of allyl bromide and 60 ml of water at pH 12 for 18 hours at 65° C. After cooling to 25° C., the solution was screened from a little insoluble material and the pH adjusted to 5.0 by addition of concentrated hydrochloric acid. The precipitated product was filtered off and dried.

EXAMPLE 2

A mixture of 1.8 g of 3-phenyl-7-(3-methyl-4-hydroxyphenyl)-2,6-dioxo-2,6-dihydrobenzo[1:2-b, 4:5-b']difuran, 1.38 g of potassium carbonate, 0.66 g allyl bromide and 20 ml of sulpholane was stirred at 120° C. for ½ hour. The mixture was cooled to 25° C., poured into water and the precipitated product filtered off, washed with water, methanol and dried.

The product 3-phenyl-7-(3-methyl-4-allyloxyphenyl)-2,6-dioxo-2,6-dihydrobenzo[1:2-b, 4:5-b']difuran dissolves in chloroform to give a red solution having an absorption maximum at 508 nm.

When applied to aromatic polyester textile materials from an aqueous dispersion the product gives very bright strong red shades with good light fastness and excellent fastness to heat and wet treatments.

EXAMPLE 3

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 1.8 g of 3-phenyl-7-(3-ethyl-4-hydroxyphenyl)-2,6-dioxo-2,6-dihydrobenzo[1:2-b, 4:5-b']difuran.

The product 3-phenyl-7-(3-ethyl-4-allyloxyphenyl)-2,6-dioxo-2,6-dihydrobenzo[1:2-b, 4:5-b']difuran dissolves in chloroform to give a red solution having an absorption maximum at 508 nm.

When applied to aromatic polyester textile materials from an aqueous dispersion the product gives very bright strong red shades with good light fastness and excellent fastness to heat and wet treatments.

EXAMPLE 4

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 1.9 g of 3-(4-hydroxyphenyl)-7-(3,5-dimethyl-4-hydroxyphenyl)-2,6-dioxo-2,6-dihydrobenzo[1:2-b, 4:5-b']difuran and 1.32 g of allyl bromide.

The product, 3-(4-allyloxyphenyl)-7-(3,5-dimethyl-4-allyloxyphenyl)-2,6-dioxo-2,6-dihydrobenzo[1:2-b, 4:5-b']difuran dissolves in chloroform to give red solution having an absorption maximum at 516 nm.

When applied to aromatic polyester textile materials from an aqueous dispersion the product gives very bright strong red shades with good light fastness and excellent fastness to heat and wet treatments.

EXAMPLE 5

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 2.0 g of 3-(4-n-propoxyphenyl)-7-(4-hydroxyphenyl)-2,6-dioxo-2,6-dihydrobenzo[1:2-b, 4:5-b']difuran.

The product, 3-(4-n-propoxyphenyl)-7-(4-allyloxyphenyl)-2,6-dioxo-2,6-dihydrobenzo[1:2-b, 4:5-b']difuran dissolves in chloroform to give a bluish-red solution having an absorption maximum at 532 nm.

When applied to aromatic polyester textile materials from an aqueous dispersion the product gives very bright strong bluish red shades with good light fastness and excellent fastness to heat and wet treatments.

EXAMPLE 6

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 1.8 g of 3-(4-methylphenyl)-7-(4-hydroxyphenyl)-2,6-dioxo-2,6-dihydrobenzo[1:2-b, 4:5-b']difuran and in place of the 0.66 g of allyl bromide there was used 0.7 g of crotyl bromide.

The product, 3-(4-methylphenyl)-7-(4-crotyloxyphenyl)-2,6-dioxo-2,6-dihydrobenzo[1:2-b, 4:5-b']difuran, dissolves in chloroform to give a red solution having an absorption maximum at 532 nm.

When applied to aromatic polyester textile materials from an aqueous dispersion the product gives bright strong red shades with good light fastness and excellent fastness to heat and wet treatments.

EXAMPLE 7

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 2.0 g of 3-(4-n-propoxyphenyl)-7-(4-hydroxyphenyl)-2,6-dioxo-2,6-dihydrobenzo[1:2-b, 4:5-b']difuran and in place of the 0.66 g of allyl bromide there was used 0.7 g of crotyl bromide.

The product, 3-(4-n-propoxyphenyl)-7-(4-crotyloxyphenyl)-2,6-dioxo-2,6-dihydrobenzo[1:2-b, 4:5-b']difuran, dissolves in chloroform to give a bluish-red solution having an absorption maximum at 532 nm.

When applied to aromatic polyester textile materials from an aqueous dispersion the product gives very bright strong bluish red shades with good light fastness and excellent fastness to heat and wet treatments.

EXAMPLE 8

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 1.8 g of beta-phenyl-7-(3-methoxy-4-hydroxyphenyl)-2,6-dioxo-2,6-dihydrobenzo[1:2-b, 4:5-b']difuran and in place of the 0.66 g of allyl bromide there was used 0.7 g of crotyl bromide.

The product, 3-phenyl-7-(3-methoxy-4-crotyloxyphenyl)-2,6-dioxo-2,6-dihydrobenzo[1:2-b, 4:5-b']difuran, dissolves in chloroform to give a bluish-red solution having an absorption maximum at 520 nm.

When applied to aromatic polyester textile materials from an aqueous dispersion the product gives strong red shades with good light fastness and excellent fastness to heat and wet treatments.

EXAMPLE 9

The procedure described in Example 2 was repeated except that in place of the 1.8 g of 3-phenyl-7-(3-methyl-4-hydroxyphenyl)-2,6-dioxo-2,6-dihydrobenzo[1:2-b, 4:5-b']difuran there was used 1.8 g of 3-(4-methylphenyl)-7-(4-hydroxyphenyl)-2,6-dioxo-2,6-dihydrobenzo[1:2-b, 4:5-b']difuran and in place of the 0.66 g of allyl bromide there was used 0.7 g of methallyl chloride.

The product, 3-(4-methylphenyl)-7-(4-[methallyloxy]-phenyl)-2,6-dioxo-2,6-dihydrobenzo[1:2-b, 4,5-b']difuran, dissolves in chloroform to give a red solution having an absorption maximum at 508 nm.

When applied to aromatic polyester textile materials from an aqueous dispersion the product gives very bright strong red shades with good light fastness and excellent fastness to heat and wet treatments.

EXAMPLE 10

The procedure described in Example 1 was repeated except that in place of the 1.13 g of 5-hydroxy-2-oxo-3-phenyl-2,3-dihydrobenzofuran there was used 1.42 g of 5-hydroxy-2-oxo-3-(4-n-propoxyphenyl)-2,3-dihydrobenzofuran. The product, 3-(4-n-propoxyphenyl)-7-(4-allyloxyphenyl)-2,6-dioxo-2,6-dihydrobenzo[1:2-b, 4:5-b']difuran, was identical to that prepared as in Example 5 and had a m.p. of 258°–259° C.

EXAMPLE 11

A mixture of 1.13 g of 3-phenyl-2-oxo-5-hydroxy-2,3-dihydrobenzofuran, 1.04 g of 4-allyloxymandelic acid, 0.95 g of p-toluene sulphonic acid and 15 ml of glacial acetic acid was stirred at 70° C. for 6 hours when 1.14 g of ammonium persulphate was added and the mixture stirred at 70° C. for ½ hour. The product was cooled to 25° C., poured into water and the precipitated solid filtered off, washed with water, methanol and dried.

The product, 3-phenyl-7(4-allyloxyphenyl)-2,6-dioxo-2,6-dihydrobenzo[1:2-b, 4:5-b']difuran, was identical to that obtained in Example 1.

In Example 11 in the place of the 15 ml of glacial acetic acid there can also be used toluene or chlorobenzene and in the place of the 0.95 g of p-toluene sul-

We claim:
1. A compound of the formula:

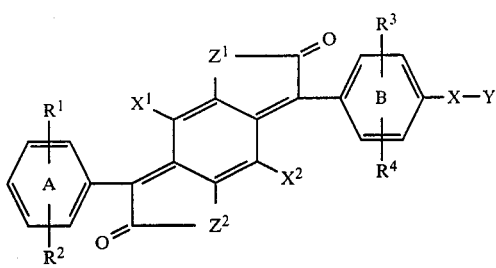

wherein,

Z$^1$ and Z$^2$ are —O—;

X$^1$ and X$^2$ are selected from H, halogen, cyano, C$_{1-4}$-aklyl, C$_{1-4}$-alkoxy, phenyl and phenyl substituted by a group selected from hydroxy, halogen, nitro, C$_{1-4}$-alkyl and C$_{1-4}$-alkyloxy, carbamoyl, sulphamoyl, or —COOL$^3$, wherein L$^3$ is selected from H, C$_{1-4}$-alkyl and phenyl;

R$^1$ to R$^4$ are each independently selected from H, C$_{1-4}$-alkyl, C$_{1-4}$-alkoxy, C$_{1-4}$-alkenyl, halogen and the group —X—Y;

X is —O— or —S—; and

Y is C$_{2-10}$-alkenyl provided that, the substitutents on rings A and B are different.

2. A compound according to claim 1 wherein X$^1$ and X$^2$ are both hydrogen.

3. A compound according to claim 1 wherein X is —O—.

4. A compound according to claim 1 wherein R$^1$ and R$^2$ are both hydrogen, both C$_{1-4}$alkyl, or R$^1$ is H and R$^2$ is C$_{1-4}$-alkyl or C$_{1-4}$-alkoxy in the para position.

5. A compound according to claim 1 wherein R$^3$ and R$^4$ are both hydrogen or both C$_{1-4}$-alkyl, or R$^3$ is H and R$^4$ is C$_{1-4}$-alkyl or C$_{1-4}$-alkoxy in an ortho position with respect to the group —X—Y.

6. A compound according to claim 1 wherein Y is C$_3$- or C$_4$-alkenyl.

7. A compound according to claim 6 wherein Y is selected from allyl, methallyl and crotyl.

* * * * *